United States Patent
Tobey

(10) Patent No.: US 9,676,624 B2
(45) Date of Patent: *Jun. 13, 2017

(54) PROCESSES FOR SELECTIVELY REDUCING THE CONCENTRATION OF HYDROGEN CYANIDE IN SYNGAS

(71) Applicant: SYNATA BIO, INC., Warrenville, IL (US)

(72) Inventor: Richard E Tobey, St. Charles, IL (US)

(73) Assignee: Synata Bio, Inc., Warrenville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,878

(22) Filed: Mar. 10, 2015

(65) Prior Publication Data

US 2015/0183639 A1 Jul. 2, 2015

Related U.S. Application Data

(63) Continuation of application No. 14/079,335, filed on Nov. 13, 2013, now Pat. No. 8,974,759, which is a continuation-in-part of application No. 13/304,902, filed on Nov. 28, 2011, now Pat. No. 8,895,274.

(51) Int. Cl.
| | |
|---|---|
| *C01B 3/50* | (2006.01) |
| *C01B 3/52* | (2006.01) |
| *B01D 53/00* | (2006.01) |
| *C12M 1/00* | (2006.01) |

(52) U.S. Cl.
CPC .............. *C01B 3/52* (2013.01); *B01D 53/00* (2013.01); *C12M 47/18* (2013.01); *C01B 2203/04* (2013.01); *C01B 2203/043* (2013.01); *C01B 2203/048* (2013.01); *C01B 2203/0415* (2013.01); *C01B 2203/0465* (2013.01); *C01B 2203/0475* (2013.01); *C01B 2203/0485* (2013.01); *C01B 2203/0495* (2013.01); *C01B 2203/061* (2013.01); *C01B 2203/062* (2013.01); *C01B 2203/146* (2013.01)

(58) Field of Classification Search
CPC ......... C01B 3/50; C01B 3/52; C01B 2203/04; C01B 2203/0415; C12M 47/18
See application file for complete search history.

(56) References Cited

U.S. PATENT DOCUMENTS

| | | | | |
|---|---|---|---|---|
| 4,189,307 | A * | 2/1980 | Marion | C01B 3/52 252/373 |
| 6,063,349 | A * | 5/2000 | Koveal, Jr. | B01D 53/14 423/236 |
| 8,128,898 | B2 * | 3/2012 | Van Dyk | B01D 53/54 423/236 |
| 8,303,849 | B2 * | 11/2012 | Hickey | B01D 53/1425 210/601 |
| 8,895,274 | B2 * | 11/2014 | Tobey | C01B 3/36 423/236 |
| 8,974,759 | B2 * | 3/2015 | Tobey | C12M 47/18 423/236 |
| 2005/0031522 | A1 * | 2/2005 | Delaney | B01D 53/62 423/419.1 |

(Continued)

*Primary Examiner* — Timothy Vanoy
(74) *Attorney, Agent, or Firm* — Cardinal Law Group

(57) ABSTRACT

This invention pertains to processes for selectively oxidizing hydrogen cyanide contained in syngas using permanganate anion as an oxidant contained in an aqueous solution that is contacted with the syngas under certain conditions of temperature, pressure and duration of contact.

20 Claims, 1 Drawing Sheet

(56) References Cited

U.S. PATENT DOCUMENTS

2009/0074643 A1* 3/2009 Pedersen ............ B01D 53/8671
　　　　　　　　　　　　　　　　　　　　　　　423/236
2012/0096770 A1* 4/2012 Van Den Born .... B01D 53/002
　　　　　　　　　　　　　　　　　　　　　　　48/197 R

* cited by examiner

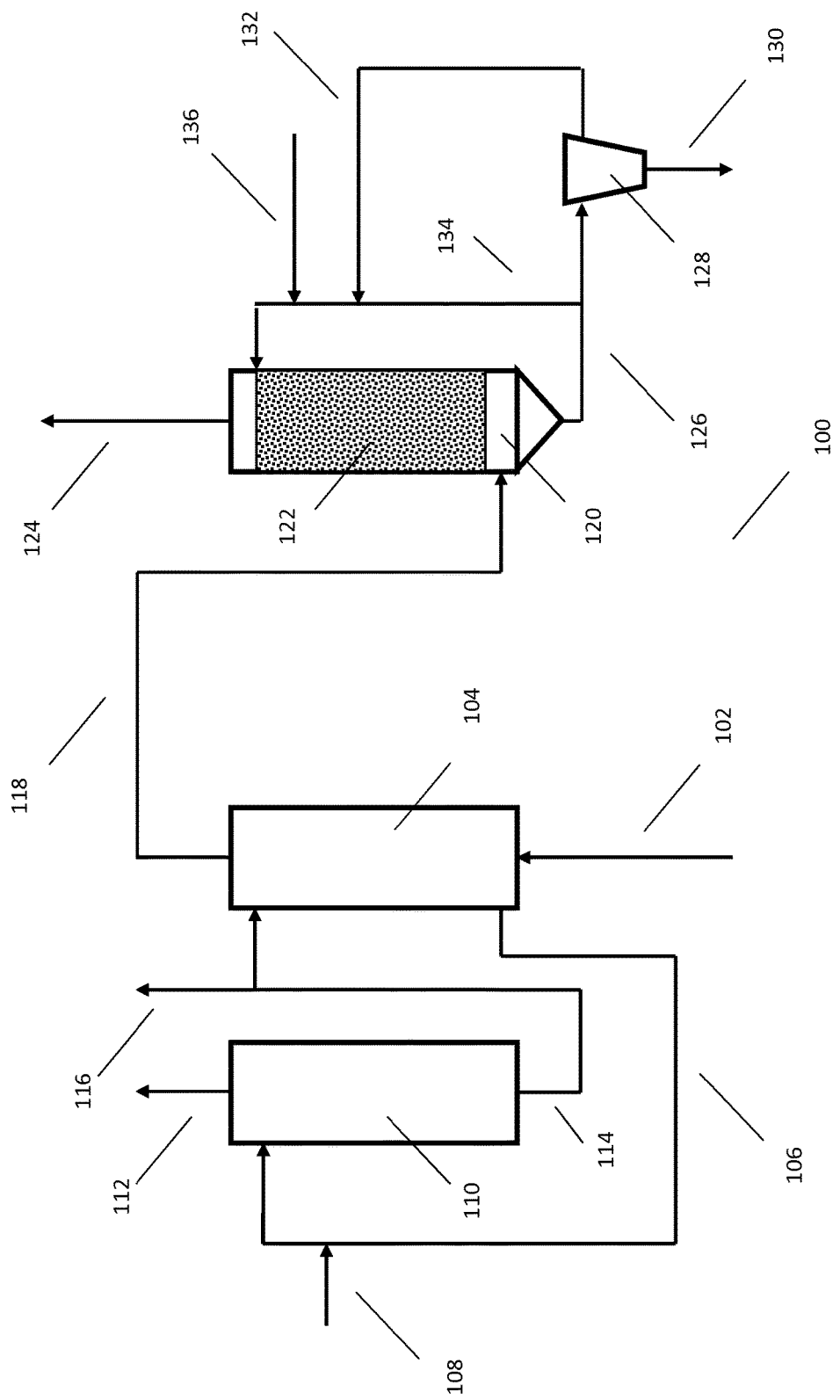

PROCESSES FOR SELECTIVELY REDUCING THE CONCENTRATION OF HYDROGEN CYANIDE IN SYNGAS

CROSS REFERENCE TO RELATED PATENT APPLICATIONS

The present application is a continuation of U.S. patent Ser. No. 14/079,335, now U.S. Pat. No. 8,974,759, filed Nov. 13, 2013, which is a continuation-in-part of U.S. patent Ser. No. 13/304,902, now U.S. Pat. No. 8,895,274, filed on Nov. 28, 2011, each being incorporated herein in their entirety by reference.

FIELD OF THE INVENTION

This invention pertains to processes for selectively reducing the concentration of hydrogen cyanide in syngas, and particularly to processes that enable permanganate anion to selectively oxidize hydrogen cyanide.

BACKGROUND

Numerous proposals exist for producing gases containing carbon monoxide, hydrogen and, optionally, carbon dioxide. For purposes herein, these gases are referred to as synthesis gas (syngas). Syngas can be produced from virtually any carbon-containing feedstock including, but not limited to, biomass and fossil fuels such as natural gas, petroleum and coal. Processes for generating syngas include, but are not limited to, gasification, partial oxidation and reforming (autothermal and steam). Other sources of the gas substrate include gases generated during petroleum and petrochemical processing and off-gases from manufacturing operations including, but not limited to, blast furnace and coke oven operations, the steel industry, non-ferrous metal industries, or captured gas from incomplete combustion processes.

Syngas can be a fuel but is often used as an intermediate for the production of other chemicals such as ammonia, methanol, and synthetic petroleum via the Fischer-Tropsch process. Syngas can also be bioconverted to produce alkanols, diols, carboxylic acids and esters, and alkanes such as methane.

Impurities in syngas generally exist due to the source of the syngas and the raw materials used to generate the syngas. Examples of impurities that can exist in syngas include, but are not limited to, acetylene, ethylene, hydrogen sulfide, carbonyl sulfide, carbon disulfide, nitric oxide, and hydrogen cyanide. Some of these impurities can be deleterious to the intended application of the syngas and accordingly must be removed. In bioprocesses, certain impurities can be inhibitors to one or more metabolic pathways or can be lethal to the microorganism. See, for instance, Xu, et al., *The Effects of Syngas Impurities on Syngas Fermentation to Liquid Fuels*, Biomass and Bioenergy, 35 (2011), 2690-2696; United States Published Patent Application No. 20110097701; Abubackar, et al., *Biological Conversion of Carbon Monoxide: Rich Syngas or Waste Gases to Bioethanol*, Biofuels, Bioproducts & Biorefining, 5, (2011), 93-114; and Munasinghe, et al., *Biomass-derived Syngas Fermentation into Biofuels: Opportunities and Challenges*, Bioresource Technology, 101, (2011), 5013-5022. Particularly deleterious impurities to microorganisms are hydrogen cyanide and acetylene. Hydrogen cyanide is also deleterious to catalysts used for Fischer-Tropsch processes.

U.S. Pat. No. 4,189,307 discloses a process for the removal of hydrogen cyanide from syngas by absorption in water. European Patent 1 051 351 B1 discloses processes for the removal of ammonia and hydrogen cyanide from syngas. In the disclosed process, hydrogen cyanide is converted to ammonia and is removed from the gas with water. A hydrocarbon gas used as the feedstock to the synthesis gas generator is used to strip ammonia out of the water. A catalytic hydrolysis or hydrogenation is used to convert the hydrogen cyanide to ammonia. It is stated at page 3 that " . . . the concentration of the combined total hydrogen and ammonia present in the syngas is preferably reduced to less than 0.1 vppm . . . " The disclosed process is complex and requires a catalyst which may be deactivated. Indeed, the patent discloses at column 5, lines 4 et seq., the use of substantially sulfur free methane.

U.S. Pat. No. 8,303,849 discloses processes for removing hydrogen cyanide from syngas using chemical and biological treatment. The process uses an aqueous scrubbing unit operation under certain conditions and then subjects the aqueous solution to microbial activity to degrade the hydrogen cyanide.

Processes are still sought to remove hydrogen cyanide from syngas, especially to concentrations of less than 1 part per million by volume in an economically attractive manner. More desirably, such processes would degrade hydrogen cyanide. Even further advantageous processes would remove other contaminants from the syngas.

SUMMARY OF THE INVENTION

It has been surprisingly found by this invention that permanganate anion, under certain conditions, can selectively oxidize hydrogen cyanide and certain other contaminants in syngas with negligible oxidation of carbon monoxide and hydrogen. The selective oxidation of hydrogen cyanide can be effected even at its typically very low concentrations in the syngas, to a concentration of below 1, preferably below 0.5 or even 0.1, part per million by volume. Yet, carbon monoxide or hydrogen, which are often in combined concentrations greater than 50 volume percent of the syngas, are only negligibly oxidized even when hydrogen cyanide is reduced to such low concentrations in the gas. The processes are particularly unexpected in that permanganate anion is known as an oxidant of carbon monoxide. See, for instance, United States Patent Application Publication No. 2012/0009109 which states at paragraph [0062] that "The CO oxidation catalyst may include various permanganate salts, e.g., silver permanganate and potassium permanganate, impregnated on a suitable support such as alumina; zinc oxide; silica; zeolite; titania; and zirconia."

It is found by this invention that a dilute solution of permanganate anion in an aqueous solution can effectively oxidize hydrogen cyanide, which hydrogen cyanide may be present in very low concentrations in the syngas, to very low concentrations, e.g., less than 1 part per million by volume, by maintaining the aqueous solution within certain pressure and temperature ranges. In its broad aspects, the processes of this invention for selectively reducing the concentration of hydrogen cyanide in a feed gas containing at least about 5 volume percent carbon monoxide and between about 1 and 500 parts per million by volume hydrogen cyanide, comprise:

a. continuously passing said gas feed into contact with an aqueous solution containing between about 50 and 2000, preferably less than about 1000, and often between about 100 and 750, parts per million by mass of permanganate anion under conditions sufficient for permanganate anion to oxidize hydrogen cyanide and generate manganese dioxide,
   i. said contacting being at a temperature of between about 4° C. and 50° C., preferably between about 10° C. and 40° C.,
   ii. said gas feed being at a pressure less than about 2000 kPa absolute, and often between about 105 and 1500 kPa, and in some instances between about 110 and 150 kPa, and
   iii. wherein the duration of said contacting is at least sufficient to provide a treated gas having a concentration of hydrogen cyanide that is less than about 30 percent of that in the gas feed, and preferably less than about 1, more preferably less than about 0.5, and most preferably less than about 0.1, part per million by volume hydrogen cyanide;
b. continuously removing said treated gas from contact with the aqueous solution;
c. intermittently or continuously replenishing permanganate anion to said aqueous solution; and
d. intermittently or continuously removing manganese dioxide from said aqueous solution.

In a preferred aspect of the invention, the parameters of temperature, pressure and duration of contact between the gas feed and the aqueous solution are such that the rate of conversion of permanganate anion per unit volume of aqueous solution to manganese dioxide is maintained at a level where the desired reduction in hydrogen cyanide concentration is obtained and the oxidation is selective. Often, less than about 100, preferably less than about 75, parts per million by mass of permanganate anion of aqueous solution are converted to manganese dioxide per second. Preferably, the duration of contact between the gas feed in an aqueous solution is less than about 30, and more frequently less than about 10, seconds.

In preferred embodiments the parameters of temperature, pressure and concentration of permanganate anion are such that the oxidation of hydrogen cyanide is mass transfer limited, i.e., the rate of oxidation of hydrogen cyanide in the aqueous solution is more rapid than the rate of mass transfer of hydrogen cyanide from the gas feed to the aqueous solution. The operation in a mass transfer-limited mode provides several advantages to the processes of this invention. First, the concentration of hydrogen cyanide in the aqueous solution remains low thereby enhancing the driving force for the mass transfer of hydrogen cyanide from the gas phase to the aqueous solution. Thus the contact time between the gas and aqueous phased is minimized for a given mass of hydrogen cyanide to be removed from the gas phase. Second, the limitation of the mass transfer of hydrogen cyanide facilitates controlling the rate of conversion of permanganate anion per unit volume aqueous solution to manganese dioxide.

In further preferred embodiments of the processes of this invention, the contact between the gas feed and aqueous solution is conducted in an absorption vessel, and aqueous solution is continuously added and withdrawn from the absorption vessel to maintain a steady state, continuous operation. Preferably, the flows of the gas feed and of the aqueous solution are countercurrent. Typically, the withdrawn aqueous solution is recycled to the absorption vessel. In order to reduce the rate of degradation of permanganate, which is catalyzed by the presence of manganese dioxide, manganese dioxide is removed from all or a portion of the aqueous solution being recycled. Manganese dioxide is a dense solid and can be removed by any suitable solids removal unit operation. Makeup permanganate anion and water can be added to the aqueous solution recycle.

An additional advantage of the processes of this invention is that certain other components contained in the gas can be selectively oxidized with negligible oxidation of carbon monoxide and hydrogen. These components include, but are not limited to, acetylene, nitric oxide and hydrogen sulfide. Acetylene and nitric oxide can adversely affect microorganisms. Interestingly, hydrogen cyanide, acetylene, nitric oxide and carbon monoxide are characterized as having triple bonds, yet carbon monoxide, despite being present in multiple magnitudes of higher concentration, is negligibly oxidized in the processes of this invention.

BRIEF DESCRIPTION OF THE DRAWING

FIG. 1 is a schematic depiction of an apparatus for practicing a process of this invention to remove hydrogen cyanide from syngas.

DETAILED DISCUSSION

Definitions

As used herein, the following terms have the meanings set forth below unless otherwise stated or clear from the context of their use.

The use of the terms "a" and "an" is intended to include one or more of the element described, and unless explicit or otherwise clear from the context, an element recited in the singular is intended to include one or more of such elements.

The term Component Composition means the composition of a gas where both water and nitrogen, although they may be present in the gas, have been excluded from the calculation of the concentration of the components. As used herein, unless otherwise stated, compositions of gases are on an anhydrous basis and exclude the presence of nitrogen.

Intermittently means from time to time and may be at regular or irregular time intervals.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous fermentation broth.

The terms selectively reducing the concentration of hydrogen cyanide and selective oxidation of hydrogen cyanide refer to selectivity in respect of carbon monoxide. The concentration of other components in the syngas can be reduced and the other components oxidized to the same, greater or lesser extent than that of hydrogen cyanide. A negligible amount of carbon monoxide can be oxidized when selectively reducing the hydrogen cyanide concentration, and preferably less than about 0.5, more preferably less than about 0.2, percent of the carbon monoxide is oxidized.

A soluble permanganate anion means that in the aqueous solution, the permanganate anion is soluble in the concentration present and under the conditions of the contacting with the gas feed. The extent of solubility can be dependent upon cations present and the temperature of the aqueous solution. Concentrations of permanganate anion in the aqueous solution are based upon the mass of the anion itself and does not include any water of hydration.

Syngas is a carbon monoxide-containing gas which preferably contains hydrogen and optionally contains carbon dioxide, and the total carbon monoxide and hydrogen Component Composition is at least about 50 percent.

Gas Feed

The gas feed used in the processes of this invention contains at least about 5 volume percent carbon monoxide and contains between about 1 and 500, and preferably between about 1 and 50 or 100, parts per million by volume hydrogen cyanide. The feed gas may contain other components and may be a syngas. Examples of other components include those that can be in a significant concentration, e.g., each being greater than 1 percent by volume such as hydrogen, carbon dioxide, nitrogen, and water vapor. Depending upon the source of the gas feed, it can contain light hydrocarbons such as methane and ethane that may be present in amounts greater than 1 percent by volume. Other components that may be present, typically in amounts less than 1 percent by volume include, but are not limited to, acetylene, ethylene, propylene, ammonia, nitric oxide, hydrogen sulfide, carbonyl sulfide, benzene, toluene, xylene, trimethylbenzene, cumene, and tars and naphthalene. The processes of this invention are particularly useful for the oxidation of acetylene, nitric oxide and hydrogen sulfide in addition to the oxidation of hydrogen cyanide.

Syngas is one source of such a gas substrate. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 70 or 75, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing. These gases may have substantially different compositions than typical syngas, and may be essentially pure hydrogen or essentially pure carbon monoxide. The gas substrate may be obtained directly from gasification or from petroleum and petrochemical processing or may be obtained by blending two or more streams. For the sake of ease of reading, the term syngas will be used herein and will be intended to include these other gas substrates.

The gas feed may be treated to remove or alter the composition including, but not limited to, removing components by chemical or physical sorption, membrane separation, and selective reaction. One optional cleanup operation is water scrubbing which may be conducted in the presence of a reactant. See, for instance, United States Published Patent Application No. 20110097701 A1, hereby incorporated by reference in its entirety. The water scrubbing also serves to remove at least a portion of other impurities from the syngas such as ethylene, acetylene, ammonia, hydrogen sulfide and carbonyl sulfide. The scrubbing may be conducted in any convenient manner. Often, the temperature of the scrubbing is in the range of about 4° C. to 50° C., and the scrubbing may be conducted at subatmospheric, atmospheric or superatmospheric pressure, e.g., frequently at about 105 to 1000 KPa absolute. Water pressure swing absorption can be used if desired. The pH of the scrubbing solution is usually maintained in the range of about 5.5 to 8, preferably between about 6 to 6.5. To the extent that oxidizable components such as, but not limited to, hydrogen cyanide and acetylene, are removed by any such treatment, the load on the permanganate oxidation is reduced thereby reducing the amount of permanganate anion required per unit volume of gas treated, and also, the control of the selective oxidation can be enhanced.

Aqueous Solution

The processes of this invention use an aqueous solution containing permanganate anion to selectively oxidize hydrogen cyanide. The permanganate anion may be supplied by any suitable water soluble salt of permanganate, and due to availability and water solubility, sodium permanganate and potassium permanganate are preferred sources of permanganate anion. As stated above, the concentration of permanganate anion is maintained in the aqueous solution in an amount less than about 2000 parts per million by mass. In general, lower concentrations of permanganate anion are preferred both because lower concentrations facilitate modulation of the selective oxidation and because permanganate is subject to degradation, particularly the presence of magnesium dioxide. The absolute amount of permanganate anion lost due to degradation is reduced with lower permanganate concentrations in the aqueous solution. The aqueous solution is preferably devoid of any undissolved permanganate compound.

During the contacting with the gas feed, permanganate anion is primarily reduced to manganese dioxide although some intermediate reduced states of manganese species may exist in the aqueous solution. Accordingly, in most instances, the concentration of permanganate in the aqueous solution will decrease with increasing contact time with the gas feed. The concentrations provided herein are intended to be initial concentrations of permanganate anion. Preferably sufficient permanganate anion is provided in the aqueous solution such that a residual concentration of permanganate anion is retained in the aqueous solution upon completion of the contact with the gas feed. This is particularly the case where it is desired to operate the process in a hydrogen cyanide mass transfer of limited mode. Often, the aqueous solution contains between about 100 and 750 parts by million by mass of permanganate anion, and the spent aqueous solution contains at least about 10, preferably at least about 50, parts by million by mass of permanganate anion.

The aqueous medium may contain additives to control pH. Other additives include those that can facilitate gas-liquid contact and mass transfer and those that can assist in the reduction of components other than hydrogen cyanide in the gas feed.

Conditions of Contacting Gas Feed with Aqueous Solution

The contact between the gas feed and aqueous solution is conducted under conditions sufficient for permanganate anion to oxidize hydrogen cyanide and generate manganese dioxide. The conditions provide a treated gas having a concentration of hydrogen cyanide that is less than about 30 percent of that in the gas feed, and preferably a treated gas contains less than about 1, more preferably less than about 0.5, and most preferably less than about 0.1, part per million by volume hydrogen cyanide. Under these conditions, other components in the gas feed, if present, such as acetylene, nitric oxide, ethylene, and hydrogen sulfide are also oxidized by the permanganate anion. In many instances, the percentage reduction of the concentration of acetylene, nitric oxide and hydrogen sulfide from the gas feed to the treated gas roughly approximates the reduction of hydrogen sulfide concentration. Accordingly, in situations where the gas feed contains one or more of acetylene, nitric oxide and hydrogen sulfide which are sought to be removed, monitoring the reduction in concentration of hydrogen cyanide frequently provides the operator in indirect indication of the effectiveness of reduction of the concentration of these other components.

The temperature at which the syngas and aqueous solution are contacted is between about 4° C. and 50° C., preferably between about 10° and 40° C. although the process can be operated at a temperature within a wide range, and is frequently used as a variable to modulate the process. For most gases having limited solubility in water, including, but not limited to, hydrogen cyanide, carbon monoxide, hydrogen, acetylene, and nitric oxide, the solubility decreases with increasing temperature. Temperature also is a factor in the kinetic rate of oxidation of a component by permanganate as well as degradation of permanganate. With increasing temperature, the reaction rate increases. Hence, the operator is able to select a temperature which provides a combination of rate of mass transfer and reaction rate that can modulate the processes of this invention. For example, where a mass transfer-limited mode of operation is sought, higher temperatures within the above range are generally used. However, if the temperature becomes too high, undue oxidation of carbon monoxide may occur and the rate of degradation of permanganate may be increased to an economically unacceptable level. Also, if the temperature is too high, the solubility of hydrogen cyanide in the aqueous solution is decreased, and thus may adversely affect the rate of mass transfer of hydrogen cyanide to the aqueous solution thereby requiring greater durations of contact in order to obtain the sought reduction in hydrogen cyanide.

The processes of this invention can use a gas feed pressure falling within a wide range. Although pressure can affect the rate of mass transfer of hydrogen cyanide to the aqueous solution, the economic viability of the processes of this invention is not dependent upon increasing the pressure of the gas feed from that at which it is supplied. Accordingly, the processes of this invention are suitable for treating gas feed supplied at a pressure less than about 2000 kPa absolute. Often the pressure is between about 105 and 1500 kPa absolute, and some instances the pressure can be in the range of about 110 to 150 kPa absolute.

The duration of contact between the gas feed and the aqueous solution is sufficient to provide a desired mass transfer of hydrogen cyanide and other oxidizable components from the gas phase to the aqueous phase. The method of contact between the gas feed and aqueous solution affects the mass transfer of hydrogen cyanide, and thus the duration of contact will be dependent upon the method used for securing the gas liquid contact. Any suitable method for securing the contact between the gas feed and aqueous solution can be used in the processes of this invention. Examples of such contact methods include the use of bubble columns, liquid spray columns, and trayed and packed (structures or random) columns which increase the surface area between the gas feed and aqueous solution per unit volume of aqueous solution. Particularly attractive apparatus for use in the processes this invention provide very low pressure drops between a pressure of the gas feed to be contacted with the aqueous solution and the pressure of the treated gas after contact with the aqueous solution. Preferably the pressure of the treated gas is within 50 kPa below the pressure of the gas feed passed to the absorption vessel.

The aqueous solution may be used in a semi-batch manner, i.e., the gas feed is passed through the aqueous solution as in a bubble column absorber, or may be flowing as in a countercurrent, co-current, or cross current absorber. The concentration of permanganate anion may be maintained by continuously or intermittently adding permanganate anion. A preferred mode of operation is using a flowing, aqueous solution that passes countercurrent to the flow of the gas feed.

The average residence time of the gas feed in contact with the aqueous solution is sufficient to enable the desired reduction in the concentration of hydrogen cyanide in the gas feed. Often the average residence time based upon the superficial gas velocity is less than about 30, preferably less than about 10, seconds providing good mass transfer exist between the gas phase and aqueous solution. As discussed above operation in a mass transfer-limited mode facilitates the mass transfer of hydrogen cyanide to the aqueous solution which enables relatively low average residence time to be achieved. The mass transfer-limited mode of operation also enables the treated gas to contain very low concentrations of hydrogen cyanide, including concentrations less than about 0.5, especially less than about 0.1, parts per million by volume.

Preferably, the pH of the aqueous solution is maintained above about 5, preferably 5.5 to 8, preferably between about 6 to 6.5, to reduce the rate of decomposition of permanganate.

In preferred modes of operation of the processes of this invention the reaction density per unit time is controlled by a combination of the mass transfer rate from the gas feed of hydrogen cyanide and other oxidizable components to the aqueous solution and the rate of oxidation of permanganate anion in the aqueous solution. The rate of oxidation of permanganate anion is determined by the oxidation of components from the feed gas as well as the autocatalytic degradation of permanganate. Frequently less than about 100, and preferably less than about 75, parts per million by mass of permanganate anion of aqueous solution is converted to manganese dioxide per second.

In the preferred operations of the processes of this invention aqueous solution is continuously added and withdrawn from the absorption zone in order to remove manganese dioxide from the aqueous solution. Manganese dioxide is believed to promote the degradation of permanganate anion. All, or a portion of, the withdrawn aqueous solution may be treated by any suitable solids separation operation including, but not limited to, filtration, centrifugation, and settling vessels to remove manganese dioxide. Frequently, the concentration of manganese dioxide in the aqueous solution contacting the gas feed is maintained less than about 250 parts per million by mass, and the mole ratio of permanganate anion to manganese dioxide is preferably greater than about 1:1, preferably greater than about 10:1. If the entire aqueous solution is not subject to the solid separation operation to remove manganese dioxide, the portion subjected to the solid separation operation should be sufficient to maintain the sought steady-state concentration of manganese dioxide in the recycled aqueous solution. Thus, the portion subjected to the solid separation operation can vary widely depending upon the rate of formation of manganese dioxide and the sought steady-state concentration of manganese dioxide in the recycled aqueous solution. Often, between about 5 and 50, say, between about 10 and 35 percent of the aqueous solution is subjected to the solid separation operation.

Makeup permanganate anion and water can be added to the absorption zone intermittently or continuously in order to maintain a steady-state operation. The makeup may be introduced into any recycle stream of aqueous solution or may be directly added to the aqueous solution in the absorption zone.

In some embodiments of the processes of this invention where the aqueous solution is continuously withdrawn from the contact with the gas feed, the aqueous solution withdrawn contains unreacted, dissolved permanganate anion. In this manner, the presence of permanganate anion enables the oxidation of hydrogen cyanide and other oxidizable components that have been removed from the gas feed to be oxidized whether it be during the time of contact between the gas feed and aqueous solution or after the aqueous solution has been withdrawn from the absorption zone. Hence, beneficial driving forces can be maintained to facilitate mass transfer of hydrogen cyanide from the gas phase and the lower the concentration of hydrogen cyanide in the treated gas, and the time elapsed after withdrawal of the aqueous solution from the absorption zone enables further oxidation of hydrogen cyanide and other oxidizable components to occur. In many instances, the concentration of permanganate anion in the withdrawn aqueous solution is at least about 50, preferably at least about 100, parts per million by mass of aqueous solution.

Use of Treated Gas the treated gas provided by the processes of this invention may be used for any suitable purpose including, but not limited to, Fischer Tropsch processes; chemical syntheses including, but not limited to, the synthesis of methanol; and as a substrate for bioconversion to a bioproduct.

As the processes of this invention serve to remove not only hydrogen cyanide but also acetylene and other components that can adversely affect the microorganisms, the treated gas is particularly useful for a feed to anaerobic bioconversion processes.

Anaerobic bioconversion processes include the production of oxygenated organic compounds. The oxygenated organic compound produced will depend upon the microorganism used for the fermentation and the conditions of the fermentation. Bioconversions of CO and $H_2/CO_2$ to acetic acid, n-butanol, butyric acid, ethanol and other products are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," (U.S. Published Patent Application No. 2007/0275447) which discloses a biologically pure culture of the microorganism *Clostridium carboxidivorans* having all of the identifying characteristics of ATCC no. BAA-624; U.S. Pat. No. 7,704, 723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 described in U.S. Published Patent Application No. 2011/0229947. All of these references are incorporated herein in their entirety.

The aqueous fermentation broth will comprise an aqueous suspension of microorganisms and various media supplements. Suitable microorganisms generally live and grow under anaerobic conditions, meaning that dissolved oxygen is essentially absent from the fermentation liquid. The various adjuvants to the aqueous fermentation broth may comprise buffering agents, trace metals, vitamins, salts etc. Adjustments in the menstruum may induce different conditions at different times such as growth and non-growth conditions which will affect the productivity of the microorganisms. Previously referenced U.S. Pat. No. 7,704,723 discloses the conditions and contents of suitable aqueous fermentation broth for bioconversion CO and $H_2/CO_2$ using anaerobic microorganisms.

The fermentation broth is maintained under anaerobic fermentation conditions including a suitable temperature, say, between 25° and 60° C., frequently in the range of about 30° to 40° C. The conditions of fermentation, including the density of microorganisms, aqueous fermentation broth composition, and fermentation zone depth, are preferably sufficient to achieve the sought conversion efficiency of hydrogen and carbon monoxide.

The fermentation conditions are preferably sufficient to effect at least about 85, preferably at least about 90, percent of the hydrogen in the substrate gas fed to the bioreactor to oxygenated organic compound. As stated above, a combination of bubble size and duration of contact with the aqueous fermentation menstruum are necessary to achieve these high conversions. However, the ease and ability to achieve these high conversions is also dependent upon having the specified electron to carbon ratios and carbon dioxide partial pressures in the substrate depleted gas phase. For commercial operations, the fermentation operation preferably provides a total molar conversion of hydrogen and carbon monoxide in the feed gas in the range of at least about 93, preferably at least about 97, mole percent. If required to provide adequate contact time between the gas bubbles and the aqueous fermentation menstruum, more than one bioreactor may be used in gas flow series in the bioreactor. The use of sequential, deep tank bubble column bioreactors is disclosed in U.S. patent application Ser. No. 13/243,062, filed on Sep. 23, 2011, herein incorporated by reference in its entirety.

Drawing

A general understanding of the invention and its application may be facilitated by reference to FIG. 1 but is not in limitation of the invention. FIG. 1 is a schematic depiction of an apparatus generally designated as 100 suitable for practicing the processes of this invention. FIG. 1 includes an optional water pressure swing absorber to treat the syngas prior to selective oxidation. FIG. 1 omits minor equipment such as pumps, compressors, valves, instruments and other devices the placement of which and operation thereof are well known to those practiced in chemical engineering. FIG. 1 also omits ancillary unit operations.

As shown, syngas is passed via line 102 to absorption 104 of a pressure swing absorption unit. Water at a temperature of about 0° C. to about 25° C., preferably between about 4° C. and 15° C., and for the purpose of this description about 7° C. is provided to absorption column 104 via line 114. Typically lower temperatures are used to minimize the amounts of carbon monoxide and hydrogen absorbed in the water. The water, if desired, can contain other components to assist in the removal of impurities from syngas. These other components include buffers and reactants such as aldehydes, hypochlorites, peroxygenates, and the like. Absorption column 104 is preferably at a pressure of between about 50 and 1500, say between about 200 and 1,000, kPa gauge. Absorption column 104 may be of any convenient absorption column design including, but not limited to, spray columns, packed and trayed columns, and bubble columns. Preferably, absorption column 104 is of a design that poses minimal pressure drop loss to the syngas. The residence time in the absorption column should be sufficient to provide a desired reduction in impurities in the syngas. When used, the pressure swing absorption unit is generally employed to reduce the hydrogen cyanide concentration in the syngas to below about 10, preferably below about 5, parts per million by volume. By reducing the hydrogen cyanide concentration, the amount of oxidant required is reduced thereby enhancing the economics of the process.

Spent water exits absorber column 104 via line 106. The spent water is passed to desorption column 110. Desorption column 110 is maintained at a lower pressure than absorption column 104, and is usually a pressure in the range of between about 5 and 200, preferably between about 50 and 110, kPa absolute. The lower pressure should be sufficient to remove at least hydrogen cyanide from the water to maintain a steady-state operation. The temperature of the water may be the same or higher or lower than the temperature of the water in absorption column 104. Makeup water is provided to desorption column via line 108. It is understood that the makeup water may be provided either to the desorption column 110 or to absorption column 104.

Desorption gases exit desorption column 110 via line 112. Line 114 returns the water for absorption to absorption column 104. A purge stream is removed from line 114 via line 116.

Syngas exits absorber column 104 via line 118 and is passed to permanganate oxidizer 120. For purpose of discussion in conjunction with this FIGURE, permanganate oxidizer 120 is a packed column containing packing 122 and has a lower conical section to facilitate the removal of manganese dioxide from the vessel. Treated syngas is withdrawn from permanganate oxidizer 120 by line 124. In permanganate oxidizer 120 the syngas is contacted with an aqueous solution of about 500 parts per million by mass of sodium permanganate. The contacting is at a temperature of about 38° C. and at a pressure substantially that of the syngas exiting absorber column 104. The aqueous solution is supplied at the top of permanganate oxidizer 120 and is withdrawn at the bottom via line 126.

The withdrawn aqueous solution contains manganese dioxide and unreacted sodium permanganate. All, or a portion of, the aqueous solution in line 126 can be passed to solids separator 128. In solids separator 128, manganese dioxide is removed. As shown, a manganese dioxide-containing stream is withdrawn from solids separator 128 via line 130, and supernatant aqueous solution having a reduced concentration of manganese dioxide is passed via line 132 as a recycle to permanganate oxidizer 120. Returning to line 126, the portion of the aqueous solution not passed to the solid separator 128 is recycled to permanganate oxidizer 120 via line 134. This portion of the aqueous solution is combined with the supernatant aqueous solution in line 132. Makeup permanganate solution is also combined with the aqueous solution being recycled in line 134 to permanganate oxidizer 120. This makeup permanganate solution is supplied via line 136 to line 134 and is a more concentrated solution of sodium permanganate sufficient to compensate for water losses via line 130 as well as replace the reacted permanganate to maintain the sought concentration of sodium permanganate in the aqueous solution passing to the top of permanganate oxidizer 120.

EXAMPLES

For purposes of illustration of the invention and not in limitation thereof the following examples based upon computer simulations are provided. All parts and percentages of solids are by mass and all parts and percentages of liquids and gases are by volume unless otherwise stated.

A permanganate oxidizer such as described in connection with the FIGURE is used to treat a syngas of the composition set forth in Table I and a syngas of the composition set forth in Table II below. The aqueous solution to the top of the permanganate oxidizer contains about 250 parts per million by mass of sodium permanganate. The permanganate oxidizer contains Beta Ring™ random packing having a nominal size of 2 inches from Koch-Glitsch, Wichita, Kans. The syngas is passed through the permanganate oxidizer to provide a residence time based on superficial velocity of about 2.7 seconds, and the aqueous solution is provided at a rate of about 0.3 liters per second per square meter of permanganate oxidizer diameter. The compositions of the treated syngas are set forth in Tables I and II.

TABLE I

| Component | Syngas | Syngas after treatment |
|---|---|---|
| H2 | 40.6% v | 40.6% v |
| CO | 44.8% v | 44.8% v |
| CO2 | 10.4% v | 10.3% v |
| C2H2 | 8.5 ppmv | 0.8 ppmv |
| C2H4 | 22.9 ppmv | 6.9 ppmv |
| H2S | 72.7 ppmv | 3.6 ppmv |
| COS | 1.2 ppmv | 1.2 ppmv |
| NH3 | 57.8 ppmv | 0.6 ppmv |
| NO | 13.1 ppmv | 5.2 ppmv |
| HCN | 5.7 ppmv | 0.1 ppmv |
| Other | balance | balance |

TABLE II

| Component | Syngas | Syngas after treatment |
|---|---|---|
| H2 | 57.7% v | 58.4% v |
| CO | 34.8% v | 35.2% v |
| CO2 | 2.4% v | 2.4% v |

TABLE II-continued

| Component | Syngas | Syngas after treatment |
|---|---|---|
| C2H2 | 5.0 ppmv | 0.5 ppmv |
| C2H4 | 15.0 ppmv | 4.6 ppmv |
| H2S | 0.0 ppmv | 0.0 ppmv |
| NO | 5.0 ppmv | 2.0 ppmv |
| HCN | 50.0 ppmv | 0.1 ppmv |
| H2O | 2.6% v | 1.5% v |
| Other | balance | balance |

As can be seen from the above Tables, virtually all the hydrogen cyanide is selectively oxidized to about 0.1 parts per million by volume, or without adversely affecting the carbon monoxide and hydrogen content of the syngases. The permanganate oxidation also oxidized acetylene, ethylene, nitric oxide and hydrogen sulfide.

It is claimed:

1. A process for selectively reducing the concentration of hydrogen cyanide with respect to carbon monoxide in a gas feed, said gas feed containing carbon monoxide and hydrogen cyanide, comprising:
   a. continuously passing said gas feed into contact with an aqueous solution of permanganate anion under conditions sufficient for the permanganate anion to oxidize the hydrogen cyanide and generate manganese dioxide, the duration of said contacting being at least sufficient to provide a treated gas having a concentration of the hydrogen cyanide that is less than that in the gas feed;
   b. continuously removing said treated gas from contact with the aqueous solution;
   c. intermittently or continuously replenishing permanganate anion to said aqueous solution; and
   d. intermittently or continuously removing manganese dioxide from said aqueous solution.

2. The process of claim 1 wherein the treated gas contains less than about 0.5 parts per million by volume of hydrogen cyanide.

3. The process of claim 2 wherein the treated gas contains less than about 0.1 parts per million by volume of hydrogen cyanide.

4. The process of claim 2 wherein the gas feed contains between about 1 and 50 parts per million by volume of hydrogen cyanide.

5. The process of claim 1 wherein the aqueous solution contains less than about 1000 parts per million by mass of permanganate anion.

6. The process of claim 1 wherein the average duration of contact between the gas feed and aqueous solution is less than about 30 seconds.

7. The process of claim 1 wherein the average duration of contact between the gas feed and aqueous solution is less than about 10 seconds.

8. The process of claim 1 wherein in step a less than about 100 parts per million by mass of permanganate anion in the aqueous solution are converted to manganese dioxide per second.

9. The process of claim 1 wherein in step a less than about 75 parts per million by mass of permanganate anion in the aqueous solution are converted to manganese dioxide per second.

10. The process of claim 1 wherein the contact between the gas feed and aqueous solution is conducted in an absorption vessel, and aqueous solution is continuously added and withdrawn from said absorption vessel.

11. The process of claim 10 wherein the contact between the gas feed and aqueous solution is countercurrent.

12. The process of claim 11 wherein the absorption vessel contains structured packing.

13. The process of claim 12 wherein the pressure of the treated gas is within 50 kPa below the pressure of the gas feed passed to the absorption vessel.

14. The process of claim 11 wherein at least a portion of the aqueous solution withdrawn from said absorption vessel is subjected to solids removal unit operation to remove manganese dioxide and is recycled to the absorption vessel.

15. The process of claim 14 wherein the solids removal unit operation comprises a centrifuge.

16. The process of claim 1 wherein the gas feed comprises at least one other impurity selected from the group of acetylene, nitric oxide and hydrogen sulfide, and at least a portion of said at least one other impurity is oxidized by permanganate anion during the contact of step (a).

17. The process of claim 1 wherein the oxidation of hydrogen cyanide in step a is mass transfer limited.

18. The process of claim 1 wherein the gas feed comprises 10 to 60 mole percent carbon monoxide.

19. The process of claim 1 wherein the duration of said contacting is at least sufficient to provide the treated gas having a concentration of the hydrogen cyanide that is about 30 percent less than that in the gas feed.

20. The process of claim 1 wherein:
   said gas feed contains at least about 5 volume percent carbon monoxide and between about 1 and 500 parts per million by volume hydrogen cyanide;
   said aqueous solution contains between about 50 and 2000 parts per million by mass of permanganate anion:
   said contacting is at a temperature of between about 4° C. and 50° C.; and
   said gas feed is at a pressure less than about 2000 kPa absolute.

* * * * *